(12) United States Patent
Roh et al.

(10) Patent No.: US 9,681,648 B2
(45) Date of Patent: Jun. 20, 2017

(54) METHOD FOR MANUFACTURING TRANSGENIC CAENORHABDITIS ELEGANS WITH DNA METHYLTRANSFERASE AND USE THEREOF

(71) Applicant: POSTECH ACADEMY-INDUSTRY FOUNDATION, Gyeongsangbuk-do (KR)

(72) Inventors: Tae Young Roh, Gyeongsangbuk-do (KR); Seung-Jae Lee, Gyeongsangbuk-do (KR); Murat Artan, Gyeongsangbuk-do (KR); Yuna Kim, Seoul (KR); Hong Gil Nam, Daegu (KR)

(73) Assignee: POSTECH ACADEMY-INDUSTRY FOUNDATION (KR)

( * ) Notice: Subject to any disclaimer, the term of this patent is extended or adjusted under 35 U.S.C. 154(b) by 0 days.

(21) Appl. No.: 14/882,977

(22) Filed: Oct. 14, 2015

(65) Prior Publication Data
US 2017/0020116 A1 Jan. 26, 2017

(30) Foreign Application Priority Data
Jul. 23, 2015 (KR) .................. 10-2015-0104475

(51) Int. Cl.
*A01K 67/033* (2006.01)
*C12N 15/01* (2006.01)
*C12N 15/85* (2006.01)

(52) U.S. Cl.
CPC ...... *A01K 67/0336* (2013.01); *C12N 15/8509* (2013.01); *A01K 2217/00* (2013.01); *A01K 2227/703* (2013.01); *A01K 2267/0331* (2013.01); *A01K 2267/0393* (2013.01); *C12N 2015/859* (2013.01); *C12N 2015/8536* (2013.01); *C12N 2015/8572* (2013.01)

(58) Field of Classification Search
None
See application file for complete search history.

(56) References Cited

U.S. PATENT DOCUMENTS

2004/0234997 A1* 11/2004 Li .................. C12N 9/1007
  435/6.12
2006/0228707 A1* 10/2006 Kenyon ............ A01K 67/0336
  435/6.1

OTHER PUBLICATIONS

Lyko et al., Mammalian (cytosine-5) methyltransferases cause genomic DNA methylation and lethality in Drosophila. Nature Gen, 1999, 23:363-366.*
Mariol et al., A rapid protocol for integrating extrachromosomal arrays with high transmission rate into the C. elegans genome. J Vis Exp. Dec. 9, 2013;(82):e50773.*
Stringham et al., Temporal and spatial expression patterns of the small heat shock (hsp16) genes in transgenic Caenorhabditis elegans. Mol Biol Cell. Feb. 1992; 3(2): 221-233.*
Zhang et al., Systematic analysis of dynamic miRNA-target interactions during C. elegans development. Development 136, 3043-3055 (2009).*
Greer et al., "DNA Methylation on N6-Adenine in C. elegans", Cell 161:4, pp. 868-878 (2015).
Hsieh, "In Vivo Activity of Murine De Novo Methyltransferases, Dnmt3a and Dnmt3b", Molecular and Cellular Biology 19:12, pp. 8211-8218 (1999).

* cited by examiner

*Primary Examiner* — Kevin Hill
*Assistant Examiner* — Arthur S Leonard
(74) *Attorney, Agent, or Firm* — Riverside Law LLP

(57) ABSTRACT

Provided are transgenic *Caenorhabditis elegans* (*C. elegans*) overexpressing DNA methyltransferase 3a (Dnmt3a) and a method of producing the same. According to the method, a specific mechanism and related factors for DNA methylation mediated by Dnmt3a may be found, and a critical gene for regulating the life span of *C. elegans* may be identified, and therefore *C. elegans* may be used as an animal model for screening a drug for a DNA methylation-related disease.

8 Claims, 5 Drawing Sheets

SEQUENCE LISTING

```
<160> NUMBER OF SEQ ID NOS: 6

<210> SEQ ID NO 1
<211> LENGTH: 917
<212> TYPE: PRT
<213> ORGANISM: Mus musculus

<400> SEQUENCE: 1

Met Pro Ser Ser Gly Pro Gly Asp Thr Ser Ser Ser Leu Glu Arg
1               5                   10                  15

Glu Asp Asp Arg Lys Glu Gly Glu Glu Gln Glu Glu Asn Arg Gly Lys
            20                  25                  30

Glu Glu Arg Gln Glu Pro Ser Ala Thr Ala Arg Lys Val Gly Arg Pro
        35                  40                  45

Gly Arg Lys Arg Lys His Pro Pro Val Glu Ser Ser Asp Thr Pro Lys
    50                  55                  60
```

```
Asp Pro Ala Val Thr Thr Lys Ser Gln Pro Met Ala Gln Asp Ser Gly
 65                  70                  75                  80

Pro Ser Asp Leu Leu Pro Asn Gly Asp Leu Glu Lys Arg Ser Glu Pro
                 85                  90                  95

Gln Pro Glu Glu Gly Ser Pro Ala Ala Gly Gln Lys Gly Gly Ala Pro
            100                 105                 110

Ala Glu Gly Glu Gly Thr Glu Thr Pro Pro Glu Ala Ser Arg Ala Val
        115                 120                 125

Glu Asn Gly Cys Cys Val Thr Lys Glu Gly Arg Gly Ala Ser Ala Gly
130                 135                 140

Glu Gly Lys Glu Gln Lys Gln Thr Asn Ile Glu Ser Met Lys Met Glu
145                 150                 155                 160

Gly Ser Arg Gly Arg Leu Arg Gly Gly Leu Gly Trp Glu Ser Ser Leu
                165                 170                 175

Arg Gln Arg Pro Met Pro Arg Leu Thr Phe Gln Ala Gly Asp Pro Tyr
                180                 185                 190

Tyr Ile Ser Lys Arg Lys Arg Asp Glu Trp Leu Ala Arg Trp Lys Arg
            195                 200                 205

Glu Ala Glu Lys Lys Ala Lys Val Ile Ala Val Met Asn Ala Val Glu
210                 215                 220

Glu Asn Gln Ala Ser Gly Glu Ser Gln Lys Val Glu Glu Ala Ser Pro
225                 230                 235                 240

Pro Ala Val Gln Gln Pro Thr Asp Pro Ala Ser Pro Thr Val Ala Thr
                245                 250                 255

Thr Pro Glu Pro Val Gly Gly Asp Ala Gly Asp Lys Asn Ala Thr Lys
                260                 265                 270

Ala Ala Asp Asp Glu Pro Glu Tyr Glu Asp Gly Arg Gly Phe Gly Ile
            275                 280                 285

Gly Glu Leu Val Trp Gly Lys Leu Arg Gly Phe Ser Trp Trp Pro Gly
290                 295                 300

Arg Ile Val Ser Trp Trp Met Thr Gly Arg Ser Arg Ala Ala Glu Gly
305                 310                 315                 320

Thr Arg Trp Val Met Trp Phe Gly Asp Gly Lys Phe Ser Val Val Cys
                325                 330                 335

Val Glu Lys Leu Met Pro Leu Ser Ser Phe Cys Ser Ala Phe His Gln
                340                 345                 350

Ala Thr Tyr Asn Lys Gln Pro Met Tyr Arg Lys Ala Ile Tyr Glu Val
            355                 360                 365

Leu Gln Val Ala Ser Ser Arg Ala Gly Lys Leu Phe Pro Ala Cys His
    370                 375                 380

Asp Ser Asp Glu Ser Asp Ser Gly Lys Ala Val Glu Val Gln Asn Lys
385                 390                 395                 400

Gln Met Ile Glu Trp Ala Leu Gly Gly Phe Gln Pro Ser Gly Pro Lys
                405                 410                 415

Gly Leu Glu Pro Pro Glu Glu Glu Lys Asn Pro Tyr Lys Glu Val Tyr
            420                 425                 430

Thr Asp Met Trp Val Glu Pro Glu Ala Ala Tyr Ala Pro Pro Pro
            435                 440                 445

Pro Ala Lys Lys Pro Arg Lys Ser Thr Thr Glu Lys Pro Lys Val Lys
    450                 455                 460

Glu Ile Ile Asp Glu Arg Thr Arg Glu Arg Leu Val Tyr Glu Val Arg
465                 470                 475                 480
```

-continued

Gln Lys Cys Arg Asn Ile Glu Asp Ile Cys Ile Ser Cys Gly Ser Leu
            485                 490                 495

Asn Val Thr Leu Glu His Pro Leu Phe Ile Gly Gly Met Cys Gln Asn
            500                 505                 510

Cys Lys Asn Cys Phe Leu Glu Cys Ala Tyr Gln Tyr Asp Asp Asp Gly
            515                 520                 525

Tyr Gln Ser Tyr Cys Thr Ile Cys Cys Gly Gly Arg Glu Val Leu Met
            530                 535                 540

Cys Gly Asn Asn Asn Cys Cys Arg Cys Phe Cys Val Glu Cys Val Asp
545                 550                 555                 560

Leu Leu Val Gly Pro Gly Ala Ala Gln Ala Ala Ile Lys Glu Asp Pro
            565                 570                 575

Trp Asn Cys Tyr Met Cys Gly His Lys Gly Thr Tyr Gly Leu Leu Arg
            580                 585                 590

Arg Arg Glu Asp Trp Pro Ser Arg Leu Gln Met Phe Phe Ala Asn Asn
            595                 600                 605

His Asp Gln Glu Phe Asp Pro Pro Lys Val Tyr Pro Val Pro Ala
            610                 615                 620

Glu Lys Arg Lys Pro Ile Arg Val Leu Ser Leu Phe Asp Gly Ile Ala
625                 630                 635                 640

Thr Gly Leu Leu Val Leu Lys Asp Leu Gly Ile Gln Val Asp Arg Tyr
            645                 650                 655

Ile Ala Ser Glu Val Cys Glu Asp Ser Ile Thr Val Gly Met Val Arg
            660                 665                 670

His Gln Gly Lys Ile Met Tyr Val Gly Asp Val Arg Ser Val Thr Gln
            675                 680                 685

Lys His Ile Gln Glu Trp Gly Pro Phe Asp Leu Val Ile Gly Gly Ser
            690                 695                 700

Pro Cys Asn Asp Leu Ser Ile Val Asn Pro Ala Arg Lys Gly Leu Tyr
705                 710                 715                 720

Glu Gly Thr Gly Arg Leu Phe Phe Glu Phe Tyr Arg Leu Leu His Asp
            725                 730                 735

Ala Arg Pro Lys Glu Gly Asp Asp Arg Pro Phe Phe Trp Leu Phe Glu
            740                 745                 750

Asn Val Val Ala Met Gly Val Ser Asp Lys Arg Asp Ile Ser Arg Phe
            755                 760                 765

Leu Glu Ser Asn Pro Val Met Ile Asp Ala Lys Glu Val Ser Ala Ala
            770                 775                 780

His Arg Ala Arg Tyr Phe Trp Gly Asn Leu Pro Gly Met Asn Arg Pro
785                 790                 795                 800

Leu Ala Ser Thr Val Asn Asp Lys Leu Glu Leu Gln Glu Cys Leu Glu
            805                 810                 815

His Gly Arg Ile Ala Lys Phe Ser Lys Val Arg Thr Ile Thr Thr Arg
            820                 825                 830

Ser Asn Ser Ile Lys Gln Gly Lys Asp Gln His Phe Pro Val Phe Met
            835                 840                 845

Asn Glu Lys Glu Asp Ile Leu Trp Cys Thr Glu Met Glu Arg Val Phe
850                 855                 860

Gly Phe Pro Val His Tyr Thr Asp Val Ser Asn Met Ser Arg Leu Ala
865                 870                 875                 880

Arg Gln Arg Leu Leu Gly Arg Ser Trp Ser Val Pro Val Ile Arg His
            885                 890                 895

Leu Phe Ala Pro Leu Lys Glu Tyr Phe Ala Cys Val Leu Gly Thr Trp

```
                      900                905              910
Gly Pro Val Glu Lys
         915

<210> SEQ ID NO 2
<211> LENGTH: 2751
<212> TYPE: DNA
<213> ORGANISM: Mus musculus

<400> SEQUENCE: 2
atgccctcca gcggccccgg ggacaccagc agctcctctc tggagcggga ggatgatcga      60
aaggaaggag aggaacagga ggagaaccgt ggcaaggaag agcgccagga gcccagcgcc     120
acggcccgga aggtggggag gcctggccgg aagcgcaagc acccaccggt ggaaagcagt     180
gacacccgca aggacccagc agtgaccacc aagtctcagc ccatggccca ggactctggc     240
ccctcagatc tgctacccaa tggagacttg agaagcgga gtgaacccca acctgaggag     300
gggagcccag ctgcagggca gaaggtgggg ccccagctg aaggagggg aactgagacc     360 ccaccagaag cctccagagc tgtggagaat ggctgctgtg tgaccaagga aggccgtgga     420
gcctctgcag agagggcaa agaacagaag cagaccaaca tcgaatccat gaaaatggag     480
ggctcccggg gccgactgcg aggtggcttg gctgggagt ccagcctccg tcagcgaccc     540
atgccaagac tcaccttcca gcagggggac ccctactaca tcagcaaacg gaaacgggat     600
gagtggctgg cacgttggaa aagggaggct gagaagaaag ccaaggtaat tgcagtaatg     660
aatgctgtgg aagagaacca ggcctctgga gagtctcaga aggtggagga ggccagccct     720
cctgctgtgc agcagcccac ggaccctgct tctccgactg tggccaccac ccctgagcca     780
gtaggagggg atgctgggga caagaatgct accaaagcag ccgacgatga gcctgagtat     840
gaggatggcc ggggctttgg cattggagag ctggtgtggg ggaaacttcg ggcttctcc     900 tggtggccag gccgaattgt gtcttggtgg atgacaggcc ggagccgagc agctgaaggc     960
actcgctggg tcatgtggtt cggagatggc aagttctcag tggtgtgtgt ggagaagctc    1020
atgccgctga gctccttctg cagtgcattc caccaggcca cctacaacaa gcagcccatg    1080
taccgcaaag ccatctacga agtcctccag gtggccagca gccgtgccgg aagctgtttt    1140
ccagcttgcc atgacagtga tgaaagtgac agtggcaagg ctgtggaagt gcagaacaag    1200
cagatgattg aatgggccct cggtggcttc agccctcgg tcctaaggg cctggagcca    1260 ccagaagaag agaagaatcc ttacaaggaa gtttacaccg acatgtgggt ggagcctgaa    1320
gcagctgctt acgccccacc cccaccagcc aagaaaccca aaagagcac aacagagaaa    1380 cctaaggtca aggagatcat tgatgagcgc acaagggagc ggctggtgta tgaggtgcgc    1440
cagaagtgca gaaacatcga ggacatttgt atctcatgtg ggagcctcaa tgtcaccctg    1500
gagcacccac tcttcattgg aggcatgtgc cagaactgta aagactgctt cttggagtgt    1560
gcttaccagt atgacgacga tgggtaccag tcctattgca ccatctgctg tggggggcgt    1620
gaagtgctca tgtgtgggaa caacaactgc tgcaggtgct tttgtgtcga gtgtgtggat    1680
ctcttggtgg ggccaggagc tgctcaggca gccattaagg aagaccctg gaactgctac    1740 atgtgcgggc ataagggcac ctatgggctg ctgcgaagac gggaagactg gccttctcga    1800
ctccagatgt ctttgccaa taaccatgac caggaatttg acccccaaa ggtttaccca    1860 cctgtgccag ctgagaagag gaagcccatc cgcgtgctgt ctctctttga tgggattgct    1920
acagggctcc tggtgctgaa ggacctgggc atccaagtgg accgctacat tgcctccgag    1980
```

```
gtgtgtgagg actccatcac ggtgggcatg gtgcggcacc agggaaagat catgtacgtc    2040
ggggacgtcc gcagcgtcac acagaagcat atccaggagt ggggcccatt cgacctggtg    2100
attggaggca gtccctgcaa tgacctctcc attgtcaacc ctgcccgcaa gggactttat    2160
gagggtactg gccgcctctt ctttgagttc taccgcctcc tgcatgatgc gcggcccaag    2220
gagggagatg atcgcccctt cttctggctc tttgagaatg tggtggccat gggcgttagt    2280
gacaagaggg acatctcgcg atttcttgag tctaaccccg tgatgattga cgccaaagaa    2340
gtgtctgctg cacacagggc ccgttacttc tggggtaacc ttcctggcat gaacaggcct    2400
ttggcatcca ctgtgaatga taagctggag ctgcaagagt gtctggagca cggcagaata    2460
gccaagttca gcaaagtgag gaccattacc accaggtcaa actctataaa gcagggcaaa    2520
gaccagcatt tccccgtctt catgaacgag aaggaggaca tcctgtggtg cactgaaatg    2580
gaaagggtgt ttggcttccc cgtccactac acagacgtct ccaacatgag ccgcttggcg    2640
aggcagagac tgctgggccg atcgtggagc gtgccggtca tccgccacct cttcgctccg    2700
ctgaaggaat attttgcttg tgtgttaggg catgggggc cggtagaaaa a             2751
```

<210> SEQ ID NO 3
<211> LENGTH: 33
<212> TYPE: DNA
<213> ORGANISM: Artificial Sequence
<220> FEATURE:
<223> OTHER INFORMATION: Chemically synthesized; forward primer

<400> SEQUENCE: 3

```
tcatctcact ggatccccag caatgccctc cag                                33
```

<210> SEQ ID NO 4
<211> LENGTH: 40
<212> TYPE: DNA
<213> ORGANISM: Artificial Sequence
<220> FEATURE:
<223> OTHER INFORMATION: Chemically synthesized; reverse primer

<400> SEQUENCE: 4

```
tcattttttc taccggcccc catgtcccta acacacaagc                         40
```

<210> SEQ ID NO 5
<211> LENGTH: 30
<212> TYPE: DNA
<213> ORGANISM: Artificial Sequence
<220> FEATURE:
<223> OTHER INFORMATION: Chemically synthesized; forward primer

<400> SEQUENCE: 5

```
gacgctctcg tggatcccca gcaatgccct                                    30
```

<210> SEQ ID NO 6
<211> LENGTH: 44
<212> TYPE: DNA
<213> ORGANISM: Artificial Sequence
<220> FEATURE:
<223> OTHER INFORMATION: Chemically synthesized; reverse primer

<400> SEQUENCE: 6

```
ggccggctag cgaattctac gaatgctatt tgtatagttc atcc                    44
```

METHOD FOR MANUFACTURING TRANSGENIC CAENORHABDITIS ELEGANS WITH DNA METHYLTRANSFERASE AND USE THEREOF

STATEMENT REGARDING GOVERNMENT RIGHTS

This invention was made with government support of Republic of Korea under Technology development and application od stem cell niche control in intestinal organoid using genome-wide analysis (1711042028) awarded by Korean Ministry of Science, ICT and Future Planning. The government has certain rights in the invention.

CROSS-REFERENCE TO RELATED APPLICATION

This application claims priority to and the benefit of Korean Patent Application No. 2015-0104475, filed on Jul. 23, 2015, the disclosure of which is incorporated herein by reference in its entirety.

BACKGROUND

1. Field of the Invention

The present invention relates to transgenic *Caenorhabditis elegans* overexpressing DNA methyltransferase 3a (Dnmt3a) and a method of producing the same.

2. Discussion of Related Art

DNA methylation is an epigenetic modification, and involved in the regulation of gene expression, the development of mammals, aging, and the biology of cancer. In mammals, DNA methyltransferases (DNMTs) serve to introduce methyl groups to the fifth carbon of cytosines ($m^5CpGs$) present in cytosine-guanine (CpG) dinucleotide sequences. Such cytosine methylation serves as an important role in gene expression by providing a binding site for proteins and altering chromatin structure between DNA and histones. An epigenetic marker generated by the DNA methylation allows genes in different tissues to maintain various gene expression patterns depending on cell type.

Also, the DNA methylation is the critical factor for forming heterochromatin, involved in various processes such as the inactivation of X-chromosomes, genetic imprinting, gene silencing, and carcinogenesis, and, as another important function, stabilizes chromosomes by silencing a transcription factor so as to protect the integrity of genomes. Abnormal DNA methylation is associated with a variety of pathological events including cancer, and generally in cancer cells, characteristics such as DNA methylation, gene-specific DNA methylation, and hypermethylation of a specific promoter are observed. Particularly, it is reported that the expression of an abnormal Dnmt gene is associated with a variety of human cancers including liver cancer, prostate cancer, and breast cancer.

Also, the methylation of a regulatory DNA base sequence closely relates with gene transcriptional activity. An unmethylated CpG island is usually observed at an activated promoter site of a tissue-specific gene. In a region of a chromatin (euchromatin) at which gene transcription actively takes place, the DNA unmethylation and histone acetylation frequently occur at a promoter and the first exon site, and the methylation of histone H3 occurs at lysine residue, the fourth amino acid of histone H3. When the CpG is methylated, gene transcription may be directly influenced by interference with binding of a transcription factor to the methylated CpG, or the binding of the transcription factor may be indirectly interfered with another protein binding to the methylated CpG as a result.

In mammals, the DNMTs are divided into four types, in which the Dnmt3 family can originally methylate CpGs, but the Dnmt1 family serves to maintain a methylation pattern during the replication of DNA. The Dnmt3 family includes Dnmt3a, Dnmt3b, and Dnmt3L, in which Dnmt3a and Dnmt3b are original methyltransferases, and Dnmt3L is a modulator.

Meanwhile, the DNA methylation is phylogenetically variable. Unlike *Arabidopsis thaliana* which has been widely researched as a model plant, it is known that DNA methylation rarely occurs in most invertebrate animal models such as yeasts, drosophilae, and *Caenorhabditis elegans* (*C. elegans*). Particularly, genes of *C. elegans* are easily manipulated and have a small size, and therefore a great number of *C. elegans* can be simultaneously grown in vitro at a relatively low cost. *C. elegans* hatches from its egg and develops into an adult through four stages including L1, L2, L3, and L4, which takes only about three days, and thus it is suitable for an animal experiment. Since *C. elegans* has a simple body structure, consists of only 959 cells except a reproductive cell, and has a transparent body, it is easy to directly observe its inside by a microscope.

Also, the cell lineage of *C. elegans* from a fertilized egg to an adult has been completely identified, and as the result of the genome project, it is known that *C. elegans* has three times as many as the number of chromosomes of a yeast and about ⅔ of the number of chromosomes of a human. 40% of the chromosomes of *C. elegans* are similar to those of the human, and *C. elegans* shares 75% of five thousand human disease genes that have been known so far. Therefore, *C. elegans* is considered a good model system for human disease research.

SUMMARY OF THE INVENTION

Accordingly, the inventors completed transgenic *C. elegans* overexpressing Dnmt3a on the assumption that *C. elegans* is able to be a good animal model to find out a complicated regulation mechanism and a pathological role of DNA methylation due to ease of genetic manipulation and unmethylation of DNA.

Therefore, the present invention is directed to providing transgenic *C. elegans* overexpressing Dnmt3a, and a method of producing the same.

However, the technical objectives to be accomplished by the present invention are not limited to the above-described objectives, and other objectives not described herein will be fully understood by those of ordinary skill in the art from the following descriptions.

In one aspect, the present invention provides transgenic *C. elegans* overexpressing Dnmt3a.

In one exemplary embodiment of the present invention, the *C. elegans* may be used as an animal model for DNA methylation-related disease research.

In another exemplary embodiment of the present invention, the DNA methylation-related disease may be cancer.

In still another exemplary embodiment of the present invention, the Dnmt3a may consist of the amino acid sequence of SEQ ID NO: 1.

In another aspect, the present invention provides a method of producing transgenic *C. elegans*, which includes (a) constructing a recombinant vector containing a Dnmt3a gene; (b) injecting the recombinant vector into *C. elegans*; and (c) irradiating the *C. elegans* with UV rays.

In one exemplary embodiment of the present invention, the Dnmt3a gene may consist of the base sequence of SEQ ID NO: 2.

In another exemplary embodiment of the present invention, the recombinant vector in operation (a) may further contain a green fluorescent protein (GFP) gene.

In still another exemplary embodiment of the present invention, the recombinant vector in operation (a) may be cloned by introducing the Dnmt3a gene and the GFP gene into a vector having a promoter of a heat-shock protein.

In yet another exemplary embodiment of the present invention, the recombinant vector in operation (a) may be cloned by introducing the Dnmt3a gene and the GFP gene into a vector having a promoter of a large ribosomal subunit.

In yet another exemplary embodiment of the present invention, the recombinant vector in operation (b) may be injected into *C. elegans* by microinjection.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
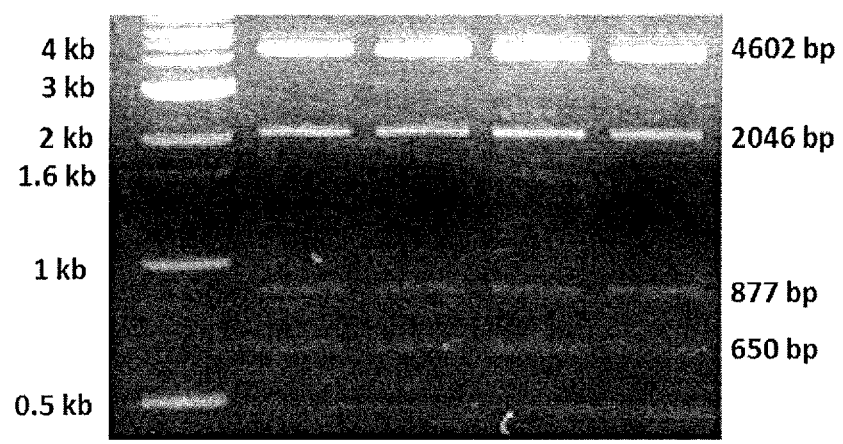
FIG. 1 shows an electrophoresis result obtained by constructing a Dnmt3a-GFP-L4455 vector by inserting Dnmt3a-GFP fusion DNA, and then treating the vector with restriction enzyme NcoI.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The present invention provides transgenic *C. elegans* overexpressing Dnmt3a, and a method of producing the same.

The term "transformation" used herein indicates that a gene introduced from an external environment is recombined and artificially inserted into a chromosome of an animal, thereby altering a part of the characteristics of the animal.

In the present invention, the transgenic *C. elegans* may be used as an animal model for studying a mechanism, regulation of a life span, and a disease, which are associated with DNA methylation, and in this case, there is no limit to a DNA methylation-related disease, which is preferably cancer.

In the present invention, a Dnmt3a protein may consist of the amino acid sequence of SEQ ID NO: 1, and a gene encoding the protein may consist of the base sequence of SEQ ID NO: 2, but the present invention is not limited thereto. That is, the Dnmt3a protein may be a polypeptide having a homology of at least about 50%, 60%, 70% or 75%, preferably at least about 80 to 90%, more preferably at least about 92 to 94%, and most preferably at least about 95%, 98%, 99% or higher with the amino acid sequence of SEQ ID NO: 1, or a polynucleotide having a homology of at least about 50%, 60%, 70% or 75%, preferably at least about 80 to 90%, more preferably at least about 92 to 94%, and most preferably at least about 95%, 98%, 99% or higher with the base sequence of SEQ ID NO: 2.

Also, the Dnmt3a protein has no limit as long as it originates from a mammal, which is preferably a human, a mouse, a rat, a dog or a pig.

Also, the present invention provides a method of producing transgenic *C. elegans*, the method including: (a) constructing a recombinant vector containing a Dnmt3a gene; (b) injecting the recombinant vector into the *C. elegans*; and (c) irradiating the *C. elegans* with UV rays.

In the present invention, the term "recombinant vector" is a vector used in genetic engineering, and preferably a plasmid vector, but the present invention is not limited thereto. For example, the recombinant vector may include a virus vector, a cosmid vector, a bacterial artificial chromosome (BAC), a yeast artificial chromosome (YAC) and other non-plasmid vectors.

In the present invention, the recombinant vector may further contain a marker gene which can be used to detect transformation, and at this time, there is no particular limit to the marker gene, which may be a gene of a fluorescent protein such as a green fluorescent protein (GFP) or a red fluorescent protein (RFP).

In the present invention, the recombinant vector may further contain a promoter for expressing a protein. Here, the term "promoter" refers to a DNA sequence regulating expression of a nucleic acid sequence operably linked to a specific host cell, has no particular limit as long as it is used for expression, and is preferably a promoter of a heat-shock protein or a promoter of a large ribosomal subunit. Also, the term "operably linked" indicates that one nucleic acid fragment is linked to another nucleic acid fragment, and therefore the function or expression thereof is influenced by the linked nucleic acid fragment.

Moreover, the recombinant vector of the present invention may further contain a random operator sequence, a sequence coding for a suitable mRNA ribosome-binding site and sequences regulating termination of transcription and translation.

The genes coding for the Dnmt3a protein and GFP, which are inserted into the recombinant vector, may be arranged to correspond to a transcription direction of a promoter present in the vector in order to effectively induce expression of each gene due to the activity of each promoter, and at this time, the Dnmt3a gene may be placed at an N terminus or C terminus of the GFP gene, and is preferably placed at the C terminus in order to effectively express a fusion protein.

Also, in the present invention, a method of injecting the recombinant vector into *C. elegans* may be any method known in the art without limitation, and is preferably microinjection with a micropipette.

Also, in the present invention, after the recombinant vector containing the Dnmt3a gene is injected into *C. elegans*, the Dnmt3a gene may be fused with its genome and irradiated with UV rays in order to establish a stable transformant throughout generations. Here, there is no limit to UV irradiation conditions, but about 300 larvae (L4 stage) which is in the stage right before reproductive cells become mature may be irradiated with energy of 300 J using a UV exposure instrument such as a UV crosslinker.

In one exemplary embodiment of the present invention, a polymerase chain reaction (PCR) was carried out, and the base sequence of the transgenic *C. elegans* was analyzed by treatment with a restriction enzyme in order to determine whether an intact Dnmt3a gene was integrated into the genome of the transgenic *C. elegans*.

Also, to determine whether the Dnmt3a protein was expressed, western blotting was carried out on a nuclear extract and a cytoplasmic extract isolated from *C. elegans*, and since the Dnmt3a gene was fused with a GFP before being injected into *C. elegans*, the DNMT3a protein was capable of being indirectly identified by detecting the GFP through fluorescent microscopy.

Also, to confirm the activity of the Dnmt3a protein, analysis of a DNA methyltransferase was carried out. In the experiment, an immunoprecipitated Dnmt3a protein and a cell lysate were used, and compared to a HeLa experimental control group, all of the two samples showed the activity of the DNA methyltransferase.

Hereinafter, exemplary examples will be provided to help in understanding of the present invention. However, the following examples are merely provided to facilitate understanding of the present invention, and the scope of the present invention is not limited to the following examples.

Example 1: Culture of *C. elegans*

As *C. elegans*, a standard wild-type Bristol strain N2 was purchased, and cultured in an *E. coli* BL21-seeded high growth agar plate at 20° C.

Example 2: Construction of Dnmt3a-GFP Recombinant Vector

As cloning vectors for constructing a Dnmt3a-GFP recombinant vector, a pPD122.18 (L4043) vector that has a promoter of an hsp-16.2 heat-shock protein, and a pPD129.59 (L4455) vector that has a promoter of a large ribosomal subunit rpl-28 were obtained from the *C. elegans* vector library provided by the Andrew Fire Group, and then cloned by the following method.

2-1. Construction of GFP-L4043 Vector

First, a pPD95.75 vector was digested with restriction enzymes BamHI and EcoRI to extract DNA from a GFP region, and the GFP DNA was inserted into the L4043 vector digested with restriction enzymes BamHI and EcoRI. Afterward, the L4043 vector containing the GFP DNA was injected to transform *E. coli* DH5α, and clones were obtained using an LB-ampicillin selective medium. Plasmid DNA extracted from the clone was treated with restriction enzyme PvuII and analyzed by electrophoresis, and therefore it was confirmed that the sizes of the digested DNA fragments were 2817 bp and 1658 bp as expected.

2-2. Construction of Dnmt3a-GFP-L4043 Vector

First, mouse Dnmt3a cDNA was obtained by amplifying a cDNA library by PCR with the following set of primers, running electrophoresis, and extracting the DNA fragment of 2727 bp from a gel.

Forward Primer:
(SEQ ID NO: 3)
5'-TCATCTCACTGGATCCCCAGCAATGCCCTCCAG-3'

Reverse Primer:
(SEQ ID NO: 4)
5'-TCATTTTTTCTACCGGCCCCCATGTCCCTAACACACAAGC-3'

A GFP-Dnmt3a-L4043 vector was constructed by digesting the GFP-L4043 vector obtained in Example 2-1 with restriction enzymes BamHI and KpnI, and inserting the Dnmt3a cDNA into the vector. Afterward, the GFP-Dnmt3a-L4043 vector was injected to transform *E. coli* DH5α, and clones were obtained using an LB-ampicillin selective medium. Plasmid DNA extracted from the clone was digested with restriction enzymes NcoI and SpeI, and therefore it was confirmed that the sizes of the digested DNA fragments were 650 bp, 1120 bp, 2046 bp, and 3319 bp as expected.

2-3. Construction of Dnmt3a-GFP-L4455 Vector

To obtain only Dnmt3a-GFP fusion DNA from the Dnmt3a-GFP-L4043 vector obtained in Example 2-2, a cDNA library was amplified by PCR with the following set of primers, and the DNA fragment of 3641 bp was extracted from a gel.

Forward Primer:
(SEQ ID NO: 5)
5'-GACGCTCTCGTGGATCCCCAGCAATGCCCT-3'

Reverse Primer:
(SEQ ID NO: 6)
5'-GGCCGGCTAGCGAATTCTACGAATGCTATTTGTATAGTTCATCC-3'

A Dnmt3a-GFP-L4455 vector was constructed by digesting the L4455 vector with restriction enzymes BamHI and EcoRI, and inserting the Dnmt3a-GFP fusion DNA into the digested L4455 vector. Afterward, the Dnmt3a-GFP-L4455 vector was injected to transform *E. coli* DH5α, and clones were obtained using an LB-ampicillin selective medium. Plasmid DNA extracted from the clone was digested with restriction enzyme NcoI, and therefore it was confirmed that the sizes of the digested DNA fragments were 650 bp, 877 bp, 2046 bp, and 4602 bp as expected (refer to FIG. 1).

Example 3: Construction and Identification of Transformant

Each of the Dnmt3a-GFP-L4043 vector and Dnmt3a-GFP-L4455 vector obtained in Example 2 (50 μg/ml), and a Pmyo-3::RFP vector (100 μg/ml) containing a promoter of a myosin heavy chain (myo-3) and an RFP were injected into wild-type *C. elegans* N2 bp microinjection, and the first generation (F1) was screened, thereby obtaining an independent transgenic animal system.

Here, the Pmyo-3::RFP vector was used as a marker for determining whether transformation is successfully carried out. To confirm the transformation performed by DNA microinjection, *C. elegans* in which the Pmyo-3::RFP gene injected with Dnmt3a exhibits strong RFP fluorescence was selected, thereby screening subjects that are successfully transformed.

Figure 2:
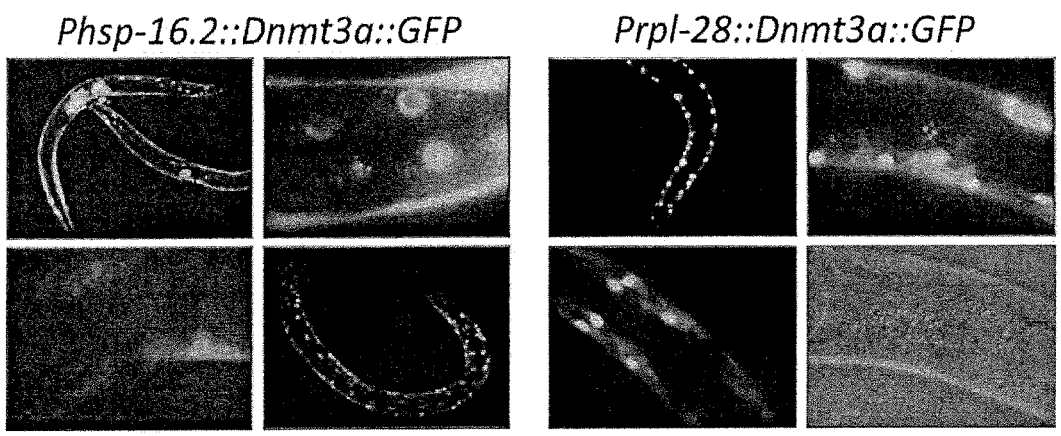
FIG. 2 shows fluorescent microscopic images obtained by injecting each of a Dnmt3a-GFP-L4043 vector (Phsp-16.2::Dnmt3a::GFP) and a Dnmt3a-GFPL4455 vector (Prpl-28::Dnmt3a::GFP) into wild-type *C. elegans* N2 and then treating the *C. elegans* N2 with heat to induce GFP expression.

That is, each of the Dnmt3a-GFP-L4043 vector (Phsp-16.2::Dnmt3a::GFP) and the Dnmt3a-GFP-L4455 vector (Prpl-28::Dnmt3a::GFP) was injected into wild-type *C. elegans* N2, and treated with heat for 15 minutes at 37° C., and as shown in FIG. 2, green fluorescence was observed by inducing expression of GFP with response to the activity of a heat-shock promoter.

In a transgenic animal using the promoter of the large ribosomal subunit rpl-28 of *C. elegans*, the Dnmt3a gene may be expressed at a subject level, but when the gene of a different organism is expressed in *C. elegans*, since it can frequently have an adverse effect on a physiological function of a subject, a vector using the promoter of the hsp16.2 protein expressed by heat shock is also constructed, thereby producing transgenic *C. elegans*.

Also, a stable transformant was induced by inserting the Dnmt3a-GFP gene into the genome of *C. elegans* by irradiating the transformant with UV rays. Here, about 300 larvae (L4 stage), which is in the stage right before reproductive cells become mature, were irradiated with energy of 300 J using a UV exposure instrument such as a UV crosslinker.

Figure 3:
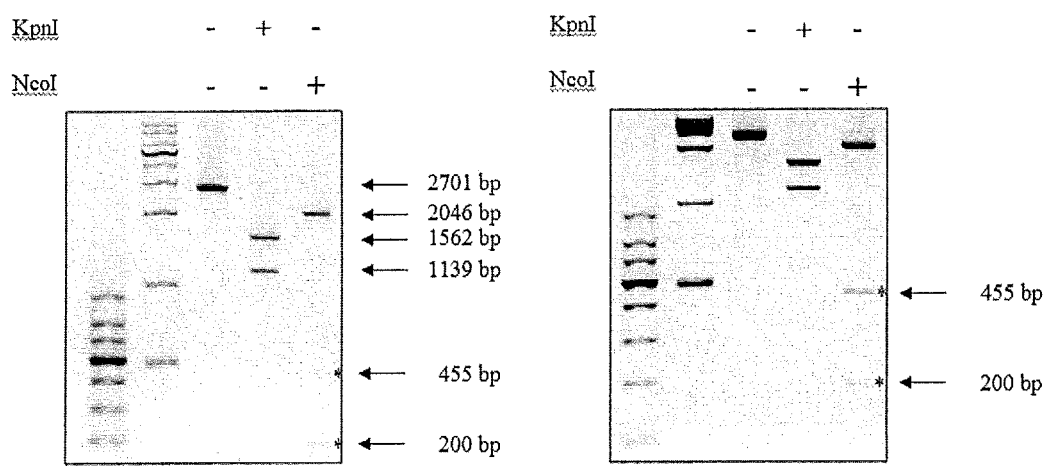
FIG. 3 shows electrophoresis results for confirming a fragment size, which are obtained by treating *C. elegans* with restriction enzymes KpnI and NcoI in order to determine whether a Dnmt3a-GFP gene is inserted into the genome of *C. elegans*.

Finally, the insertion into the genome was confirmed by the restriction enzymes (KpnI, NcoI) fragment sizes produced after PCR amplification, and the result is shown in FIG. 3.

Example 4: Confirmation of Dnmt3a Protein Expression

Western blotting was carried out to determine whether an actual Dnmt3a-GFP fusion protein was expressed in the transgenic *C. elegans* (Prpl-28::Dnmt3a::GFP) produced in Example 3.

Particularly, a protein was extracted from *C. elegans* by a known method, and identified with an anti-Dnmt3a antibody and an anti-GFP antibody (Abiocode Inc.), and here, as a control group, a HeLa cell line transformed with the GFP gene was used.

Figure 4:
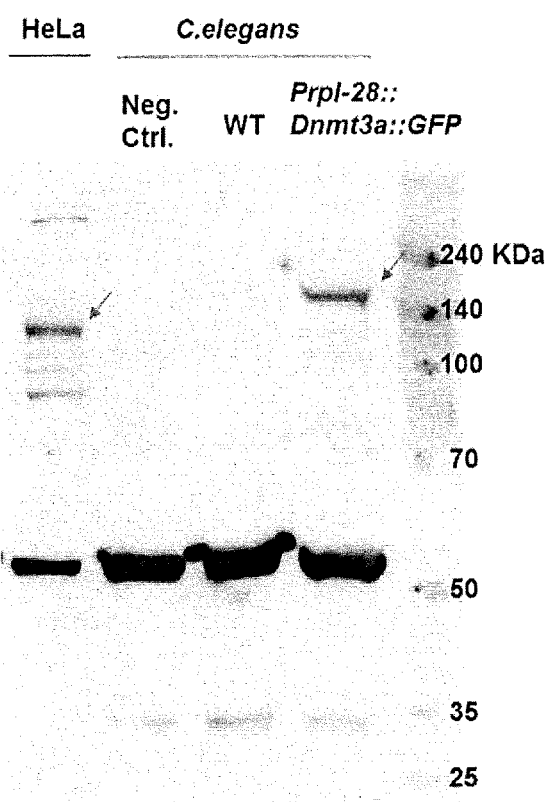
FIG. 4 shows western blotting results to determine whether a Dnmt3a-GFP fusion protein is expressed in the transgenic *C. elegans* (Prpl-28::Dnmt3a::GFP) of the present invention.

Consequently, as shown in FIG. 4, the expression of the Dnmt3a-GFP fusion protein was observed in transgenic *C. elegans* (Prpl28::Dnmt3a::GFP) (indicated by the red arrow). That is, the Dnmt3a-GFP fusion protein was observed at a position corresponding to a larger size than the size of the GFP protein observed in the control group.

Example 5: Confirmation of Activity of Dnmt3a Protein

It was confirmed whether the activity of an actual Dnmt3a protein was maintained in the transgenic *C. elegans* (Prpl-28::Dnmt3a::GFP) produced in Example 3.

Particularly, the activity of Dnmt3a was measured using an EpiQuik™ DNA methyltransferase activity/inhibition assay kit (P-3001, Epigentek, USA). That is, DNA with a high content of cytosine was allowed to react with a cell lysate (10 µg) by which the expression of Dnmt3a was confirmed or immunoprecipitated Dnmt3a protein (12 µg), and methylated cytosine was confirmed with an anti-5-methylcytosine antibody (Epigentek). Here, a coloring solution was added to measure an optical density according to color variation, thereby allowing the comparison of the activity of Dnmt3a, and as a control group, a HeLa cell line having the activity of Dnmt3a was used.

Figure 5:
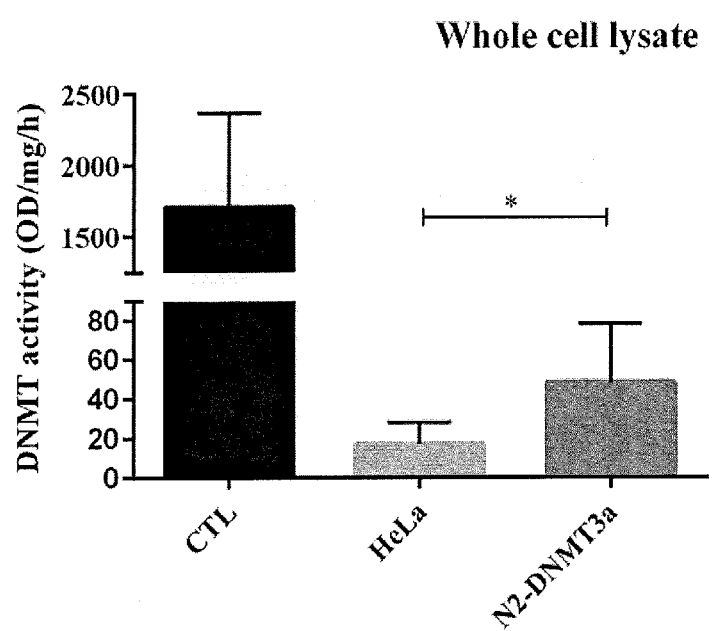
FIG. 5 shows optical densities of the transgenic *C. elegans* (Prpl-28::Dnmt3a::GFP) of the present invention in order to determine whether the activity of a Dnmt3a protein is actually maintained.

As a result, the immunoprecipitated Dnmt3a of the present invention was expressed in the HeLa cell line, and thus had a similar activity to the immunoprecipitated Dnmt3a (control group). As shown in FIG. 5, in the activity confirming experiment using a cell lysate, the immunoprecipitated Dnmt3a of the present invention showed a higher activity than that of the HeLa cell line as the control group.

By using an animal model of the present invention, specific mechanisms and related factors for DNA methylation mediated by Dnmt3a can be understood.

Also, according to the present invention, since it is possible to define the relevance between DNA methylation and regulation of a life span, a critical gene for regulating the life span of *C. elegans* can be identified.

Also, according to the present invention, since it is possible to define the relevance between DNA methylation and a disease, mechanisms of the occurrence of various diseases such as cancer are found, and therefore *C. elegans* can be used as an animal model for drug screening in order to develop an anticancer agent.

It would be understood by those of ordinary skill in the art that the above descriptions of the present invention are exemplary, and the example embodiments disclosed herein can be easily modified into other specific forms without changing the technical spirit or essential features of the present invention. Therefore, it should be interpreted that the example embodiments described above are exemplary in all aspects, and are not limitative.

---

What is claimed is:

1. Transgenic *Caenorhabditis elegans* (*C. elegans*) which overexpresses DNA methyltransferase 3 (Dnmt3), wherein the Dnmt3 consists of the amino acid sequence of SEQ ID NO: 1.

2. A method of producing transgenic *Caenorhabditis elegans* (*C. elegans*) of claim 1, the method comprising:
   (a) constructing a recombinant vector containing a DNA methyltransferase 3 (Dnmt3) gene wherein the Dnmt3 gene consists of the nucleic acid sequence of SEQ ID NO: 2;
   (b) injecting the recombinant vector into the *C. elegans*; and
   (c) irradiating the *C. elegans* with UV rays.

3. The method of claim 2, wherein the recombinant vector in the step (a) further contains a green fluorescent protein (GFP) gene.

4. The method of claim 2, wherein the recombinant vector in the step (a) is cloned by introducing the Dnmt3 gene and a GFP gene into a vector having a promoter of a heat-shock protein.

5. The method of claim 2, wherein the recombinant vector in the step (a) is cloned by introducing the Dnmt3 gene and a GFP gene into a vector having a promoter of a large ribosomal subunit.

6. The method of claim 2, wherein the recombinant vector in the step (b) is injected into the *C. elegans* by microinjection.

7. A method of using a transgenic *Caenorhabditis elegans* (*C. elegans*) which overexpresses DNA methyltransferase 3 (Dnmt3), wherein the Dnmt3 consists of the amino acid sequence of SEQ ID NO: 1 in an animal model for studying a DNA methylation-related disease.

8. The method of claim 7, wherein the DNA methylation-related disease is cancer.

* * * * *